(12) United States Patent
Rohith et al.

(10) Patent No.: US 12,740,774 B2
(45) Date of Patent: Sep. 22, 2026

(54) SKIN FLAP RETRACTION DEVICE

(71) Applicant: DESSINRX HEALTHCARE PVT. LTD, Hyderabad (IN)

(72) Inventors: Gorrepati Rohith, Hyderabad (IN); Gorrepati Vivek, Hyderabad (IN); Devyani Singhi, Hyderabad (IN)

( * ) Notice: Subject to any disclaimer, the term of this patent is extended or adjusted under 35 U.S.C. 154(b) by 0 days.

(21) Appl. No.: 18/855,647

(22) PCT Filed: Apr. 10, 2023

(86) PCT No.: PCT/IN2023/050344
§ 371 (c)(1), (2) Date: Oct. 10, 2024

(87) PCT Pub. No.: WO2023/199347
PCT Pub. Date: Oct. 19, 2023

(65) Prior Publication Data

US 2025/0248701 A1 Aug. 7, 2025

(30) Foreign Application Priority Data

Apr. 10, 2022 (IN) ............................ 202241021395

(51) Int. Cl.
*A61B 17/02* (2006.01)

(52) U.S. Cl.
CPC ...... *A61B 17/0206* (2013.01); *A61B 17/0218* (2013.01)

(58) Field of Classification Search
CPC .......... A61B 2017/00477; A61B 17/02; A61B 17/0208; A61B 17/0206; A61B 17/0287
See application file for complete search history.

(56) References Cited

U.S. PATENT DOCUMENTS

2004/0002631 A1* 1/2004 Wu .................... A61B 17/0206 600/210
2005/0192484 A1* 9/2005 Sharratt ............. A61B 17/0293 600/210
2006/0211920 A1* 9/2006 Bethke ............... A61B 17/0206 600/234
2010/0191253 A1* 7/2010 Oostman, Jr. ...... A61B 17/0206 606/1
2015/0057713 A1* 2/2015 Iott .................... A61B 17/7085 606/86 A
2021/0275159 A1* 9/2021 Harper ................... A61B 90/57

FOREIGN PATENT DOCUMENTS

CN 213189822 U 5/2021
CN 214761240 U 11/2021
WO WO-2018046916 A1 * 3/2018 ............ A61B 17/02

* cited by examiner

*Primary Examiner* — Eduardo C Robert
*Assistant Examiner* — Holly Joanna Lane
(74) *Attorney, Agent, or Firm* — Rahman LLC

(57) ABSTRACT

Skin flap retraction device. The self-retaining retractor device (100) can provide appropriate, adequate, and dynamic traction during a surgical procedure that involves skin flap elevation. The self-retaining dynamic surgical retractor device (100) employs a precurved detachable solid block (20) and malleable arm assembly (22 and 24) that can be used for various surgeries involving raising skin flaps and places that need a dynamic yet gentle traction, for example, during a mastectomy procedure, which typically requires raising of skin flaps.

6 Claims, 7 Drawing Sheets

SKIN FLAP RETRACTION DEVICE

TECHNICAL FIELD

The present invention relates medical and surgical devices. The present invention also relates to methods and systems for skin flap retraction. Further, the invention relates to surgical retractors. Further, the present invention specifically relates to an improved skin flap retraction device for providing adequate and dynamic traction in skin flap elevation and surgical procedures.

BACKGROUND OF THE INVENTION

A skin flap is healthy skin and tissue that is partly detached from an underlying structure and a chunk of diseased tissue is removed or is otherwise usually moved to cover a nearby wound. A skin flap may contain skin and fat, or skin, fat, and muscle. The subcutaneous layer (or deeper layer depending on the type of surgery) is incised and the skin along with subcutaneous fat is lifted off from the underlying tissue in a surgical procedure. The edge(s) of the skin is retracted, and a vertical/inclined traction is provided by the assistants using a skin-hook retractor device. The entire underlying tissue will be separated from the skin flap using an electrocautery/harmonic scalpel device depending on the surgeon's preference.

It is to be noted that maintaining the traction in the skin is important in the surgical procedures without which, the plane of dissection will be missed, resulting in thinner or thicker flaps. Either of these flaps is prone for ischemia due to inadequate blood supply resulting in flap necrosis. The discussed problem can be very severe in surgeries such as ilio-inguinal block dissection, where the rates soar as high as 27-85%. Also, there are chances of leaving large amounts of fat globules attached to the skin flap resulting in postoperative seroma formation. The complication is seen in 30% of the patients who undergo mastectomy in which skin flaps are elevated.

Surgical retractors are generally designed for providing adequate visual and operative access to the surgical field for the operating surgeon. Traditional retraction systems usually require one or more assistants to retract the tissues away from the surgical field for adequate exposure.

Rigid hand-held traditional retractors are the most used retractors in almost all the surgeries in one step or the other. Such devices require continuous manipulation in terms of direction and force applied. In most of the cases, the assistant, although a skilled surgeon, would not get an adequate exposure to the surgical field. It is a tedious task and many a time, interferes with the operating surgeon's efficiency thereby prolonging operative time. Tension applied at various places would be unequal resulting in a faulty thickness of the flap, resulting in flap necrosis and other complications.

Various self-retaining retractors have been designed and developed in the recent past but have not been widely used due to the limitations the design and various other reasons. Majority of the prior art devices are mounted over the operating table to enable retraction. But the size and rigid framework of such prior art devices make them cumbersome to use in surgical procedures. Such devices are further complicated and require multiple parts. Problems such as need for frequent realigning and repositioning when dislodged precluded their success. Additionally, human breast varies in its size, shape, volume, and laxity. It is difficult for a single rigid retracting assembly to be used in all the cases with equal ease and efficiency.

In one embodiment of prior art a manually held skin-hook retractor is proposed to give traction force on the skin flap. The operating surgeon gives counter-traction with his left hand while dissection is carried out with an energy device held in his right hand. The proposed device requires the assistant to hold the skin hooks for a prolonged period of time.

In another embodiment of prior art, eyebrow retractors have also been utilized in breast surgery, which have a stainless-steel retractor ring and elastic hooks. However, the retractor ring is rigid and cannot be used only for the upper flap. It is difficult to use as it has a fixed structure, but the structure of the breast varies from person to person to a large extent. So, thereby manual retraction using assistants is the preferred method for skin flap rising.

Based on the foregoing, it is believed that a need exists for an improved self-retaining retractor system that can provide appropriate, adequate and dynamic traction during a surgery that involves skin flap elevation. Also, a need exists for an improved skin flap retraction device for providing adequate and dynamic traction in skin flap elevation and surgical procedures, as described in greater detail herein.

SUMMARY OF THE INVENTION

The following summary is provided to facilitate an understanding of some of the innovative features unique to the disclosed embodiment and is not intended to be a full description.

It is, therefore, one aspect of the disclosed embodiments to provide for an improved skin retractor device and method.

It is another aspect of the disclosed embodiments to provide for an improved self-retaining retractor system that can provide appropriate, adequate and dynamic traction during a surgery that involves skin flap elevation.

It is further aspect of the disclosed embodiments to provide for an improved skin flap retraction device for providing adequate and dynamic traction in skin flap elevation and surgical procedures.

A skin flap retraction device (100) is disclosed herein. The skin flap retraction device (100) can provide appropriate, adequate, and dynamic traction during a surgical procedure that involves skin flap elevation. The skin flap retraction device (100) employs a pre-curved detachable central solid block (20) and malleable arms (22 and 24) that can be used for various surgeries involving raising skin flaps and places that need a dynamic yet gentle traction, for example, during a mastectomy procedure, which typically requires raising of skin flaps.

The skin flap retraction device (100) comprises the pre-curved detachable central solid block (20) with a first malleable (or deformable or bendable) arm (22) and a second malleable arm (24). The first malleable arm (22) and the pre-curved detachable central solid block (20) are coupled at an end (18) of the first malleable arm (22) and a first respective end (16) of the pre-curved detachable central solid block (20) thereof via a first coupling assembly (28) and is secured using a screw (32) or any kind of fasteners.

The second malleable (or deformable or bendable) arm (24) and the pre-curved detachable central solid block (20) are coupled to one another at an end (26) of the second malleable arm (24) and a second respective end (14) of the pre-curved detachable central solid block (20) thereof via a second couple assembly (30) and secured using a screw (34). The skin flap retraction device (100) is mounted on a base plate (36).

DETAILED DESCRIPTION

The values and configurations discussed in these non-limiting examples can be varied and are cited merely to illustrate at least one embodiment and are not intended to limit the scope thereof.

The embodiments now will be described more fully hereinafter with reference to the accompanying drawings, in which illustrative embodiments of the invention are shown. The embodiments disclosed herein can be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout. As used herein, the term "and/or" includes all combinations of one or more of the associated listed items.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Proposed Technical Advancement: The proposed skin flap retraction device (100) seeks to achieve an improved device which mitigates or reduces the problems associated with elevation of skin flaps in a surgery. The skin flap retraction device (100) further obviates the need for manual retraction by an assistant surgeon thereby improve a surgeon's exposure to the ongoing surgery. The skin flap retraction device (100) provides a simple yet effective retractor with improvised dynamic retractor with self-retaining properties.

Figure 1:
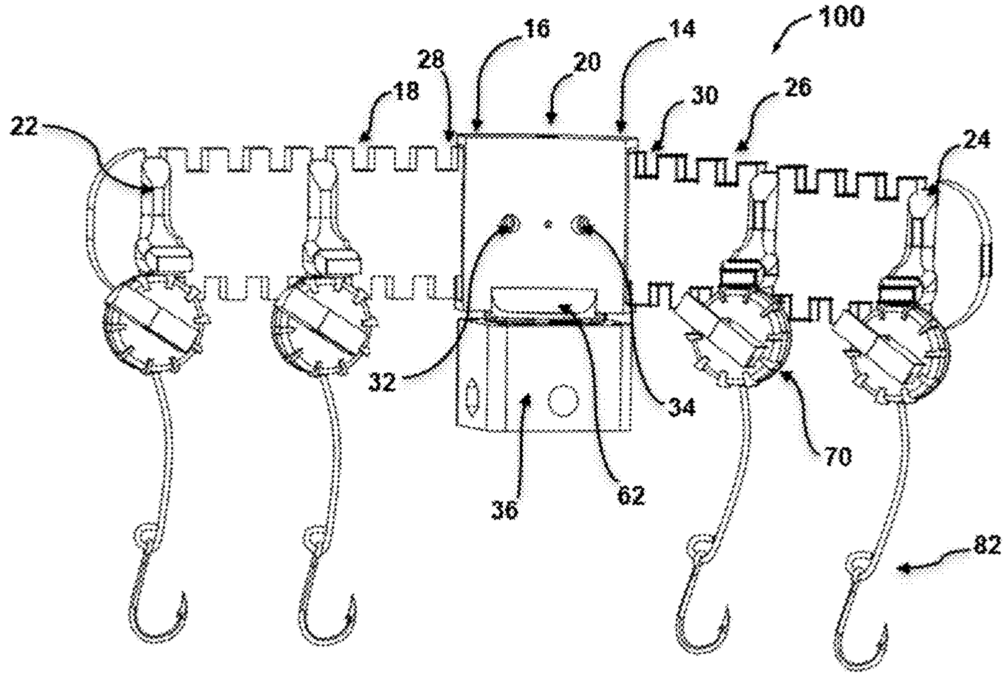
FIG. 1-9 illustrate embodiments of the skin flap retraction device (100) of the present invention and its various components.
Figure 2:
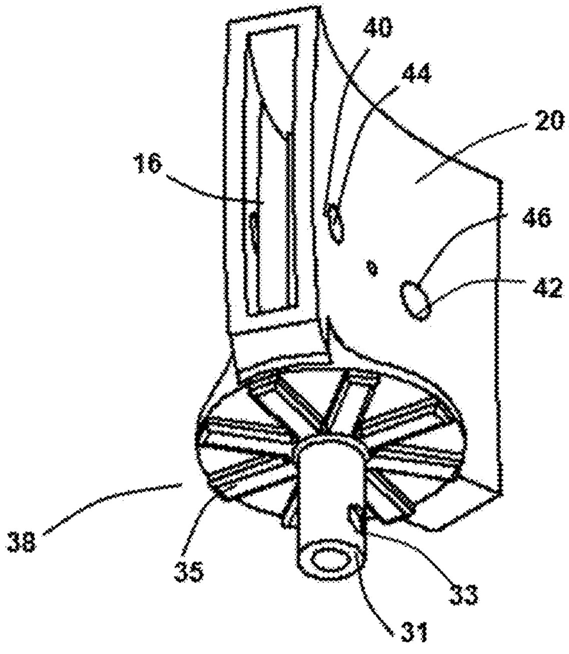
Figure 3:
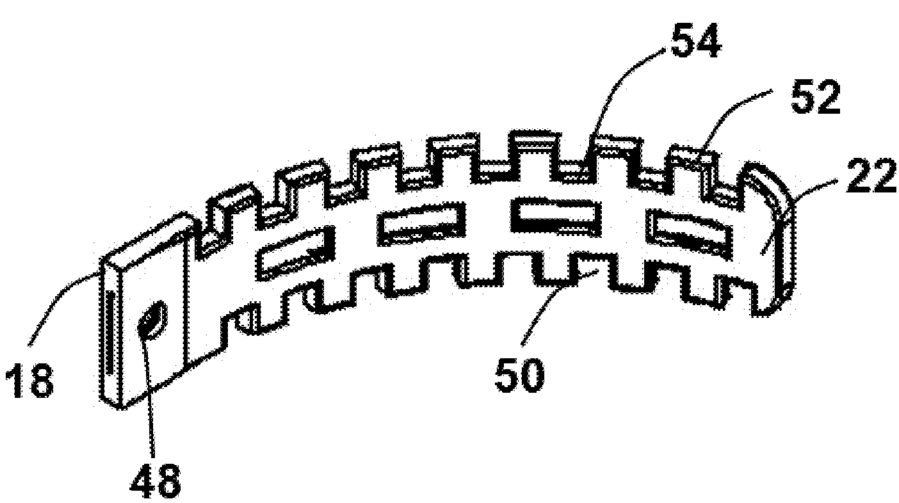

Detailed Description of the Invention: Referring to FIGS. 1-3, a skin flap retraction device (100) is depicted. This skin flap retraction device (100) includes a pre-curved detachable central solid block (20) with a first malleable (deformable or bendable) arm (22) and a second malleable arm (24). The first malleable arm (22) and the pre-curved detachable central solid block (20) are coupled to one another at an end (18) of the first malleable arm portion (22) and a first respective end (16) of the pre-curved detachable central solid block (20) thereof via a first coupling assembly (28) and is secured using a screw (32).

The second malleable (deformable or bendable) arm (24) and the pre-curved detachable central solid block (20) are coupled to one another at an end (26) of the second malleable arm (24) and a second respective end (14) of the pre-curved detachable central solid block (20) thereof via a second coupling assembly (30) and secured using a screw (34). The entire re-curved detachable central solid block (20) is mounted on a base plate (36). Arcuate shape of the skin flap retraction device (100) can be best appreciated in FIG. 1.

The pre-curved detachable central solid block (20) can be best appreciated in FIG. 2. The pre-curved detachable central solid block (20) has a rotatable shaft coupling system (38) at its base and the base plate (36) with one or more rotational stoppers (35) on its superior surface which can accommodate the rotatable shaft coupling system (38) present on the base of the pre-curved detachable central solid block (20). On either of its sides, the pre-curved detachable central solid block (20) has the first respective end (16) and the second respective end (14) that can accommodate malleable arms (22 and 24). On its posterior aspect, two holes (40 and 42) are provided that are used to secure the malleable arms (22 and 24) to the pre-curved detachable solid block (20) using screw (32, 34). Circular threadings (44 and 46) with equal pitch throughout its length is engraved on inner aspects of the two holes (40 and 42). The pre-curved detachable central solid block has a peg like elevation (31) with a key hole (33) and the one or more rotational stoppers (35) The pre-curved detachable central solid block (20) is preferably made of stainless steel or surgical grade plastic, a titanium alloy, or the like. Other suitable material with the required rigidity and strength can also be used.

The malleable arms (22 and 24) are preferably relatively flat and assume an arc shape (FIGS. 3 and 4) but they may, however be fabricated to other shapes resulting in semi-circular configuration, irregular configuration, or other configurations.

Each of the malleable arms (22 and 24) has the end (18, 26) that can be accommodated into the first respective end (16) or the second respective end (14) of the pre-curved detachable central solid block (20) respectively. In the centre of the end (18, 16), there is a hole (48, 68) that can be used to immobilize each of the malleable arms (22 and 24) and the pre-curved detachable central solid block (20) using the screw (32, 34). Each malleable arms (22 and 24) is preferably made of stainless steel, copper, or the like. Other material with sufficient strength and thickness which provides both stability and malleable property to the instrument can also be used.

Figure 4:
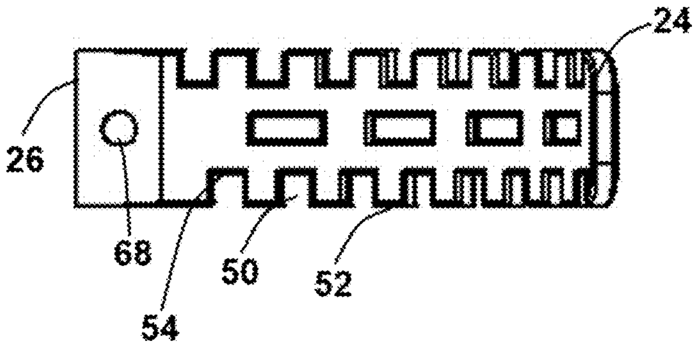

The skin flap retraction device (100) includes a plurality of pitches or notches (50) made on the malleable arms (22 and 24) (FIGS. 3 and 4). The plurality of notches or pitches (50) are equally spaced about the malleable arms (22 and 24) on both upper and lower edges (52 and 54) of the plurality of notches or pitches (50). The plurality of notches or pitches (50) are used to affix or clip torsion spring systems (e.g., spiral torsion spring system (70) that are discussed below), onto the malleable arms portions (22 and 24).

Figure 5:
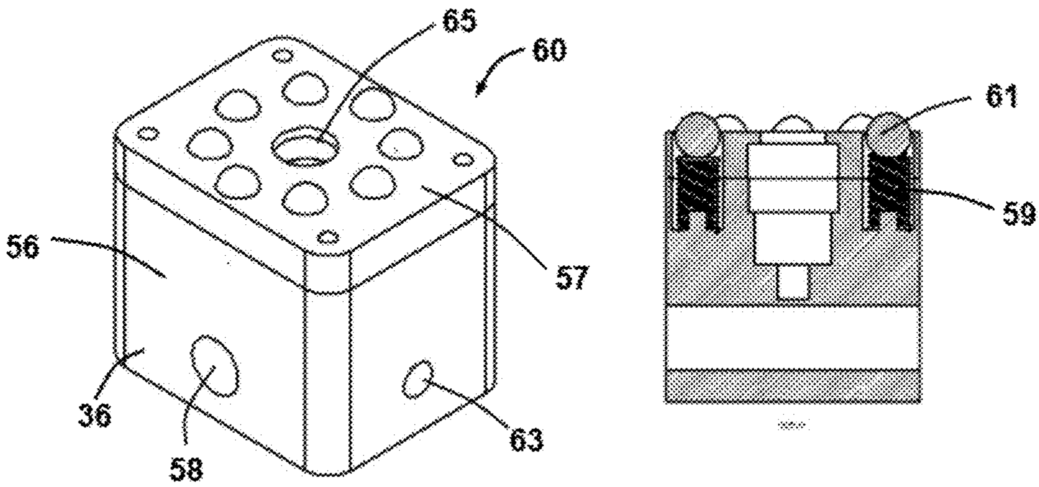

The skin flap retraction device (100) has a base plate (36) (See FIG. 5) on which the pre-curved detachable central solid block (20) rests. The base plate (36) has a body (56) with one or more spring (59), ball (61) sets and a cap (57). There is a socket (65) which is passing through the cap (57) into the body (56) and which is complementary to the peg (31) on the base of the pre-curved detachable central solid block (20). The pre-curved detachable central solid block (20) can be placed facing any direction by utilizing the peg and socket joint (62) formed by the base plate (36) and the pre-curved detachable central solid block (20). The body (56) necessarily has a central circular hole (58) extending throughout a length of the body (56). The body (56) has a central circular hole (58) which snuggly fits and glides over a support metallic arm that is used to mount the skin flap retraction device (100) and rigidly secured to an operating table. A knob screw can be placed in a threaded holed (63) which is perpendicular to the central circular hole (58) of the body (56) to tighten the skin flap retraction device (100) on the support metallic arm.

Figure 6:
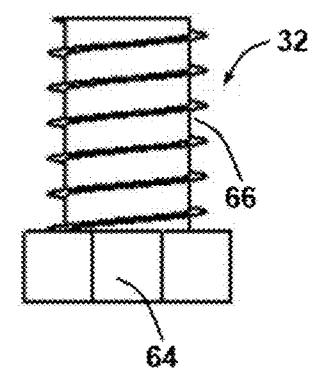

Each of the malleable arms (22 and 24) are attached to the pre-curved detachable central solid block (20) using the screw (32, 34). Each of the screw (32, 34) has a head (64) and a shank (66) (of which the screw 32 is illustrated in FIG. 6) with threading throughout its length with equal pitch.

Figure 7:
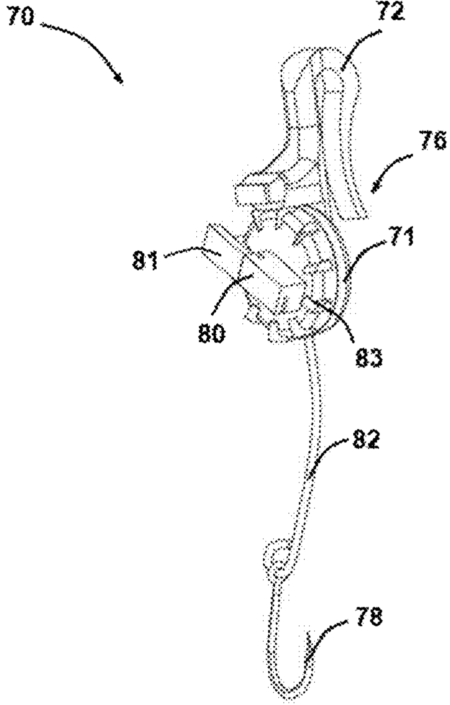

FIG. 7 depicts a spiral torsion spring system (70) that is used to elevate skin flap. The spiral torsion spring system (70) has an elastic/rigid cable (82) with a first end of it attached to a torsion spring (76) and a metallic hook (78) on a second end. The metallic hook (78) can be inserted into the subcuticular layer of skin preventing its dislodgement. The spiral torsion spring system (70) has a tension key (80) on a flat surface (71) which can be used to increase or decrease a tension of the torsion spring at a given particular point of time. One or more unidirectional stoppers (83) is located on an anterior surface of the flat surface (71) to hold the tension at the given particular point of time. A split key (81) can be lifted up and rotated anti clockwise to decrease the tension in the flat surface (71).

Figure 8:
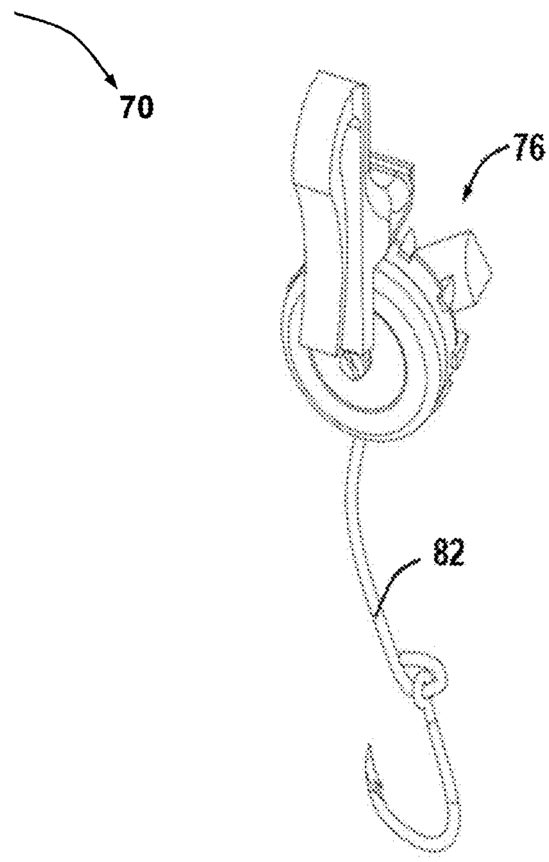
Figure 9:
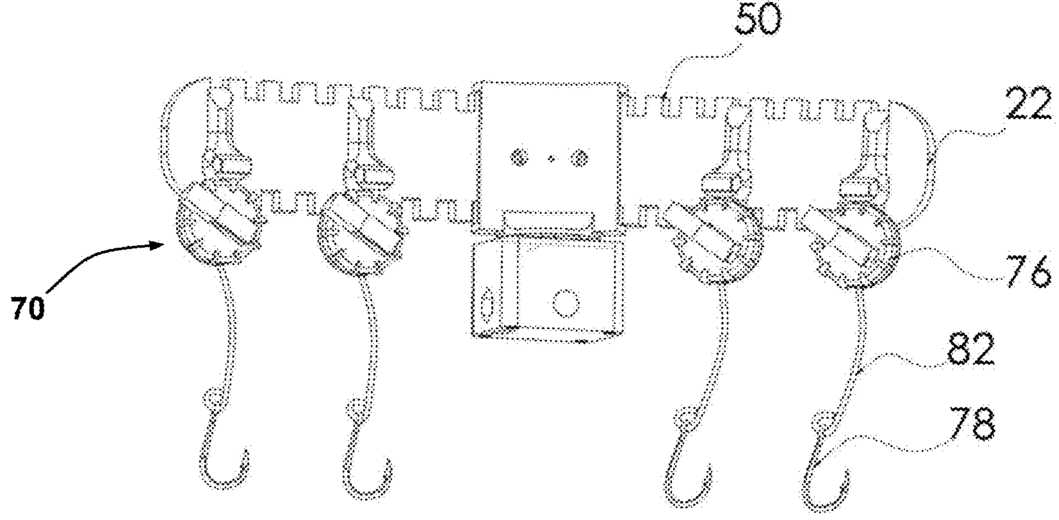

FIG. 8 represents another perspective view of the spiral torsion spring system (70) with which variable stress and length can be provided to the skin flap. The spiral torsion spring system (70) can be reversibly attached to the malleable arms (22 and 24) at each of the plurality pitches or notches (50). The pre-curved detachable central solid block (20) attachment to the malleable arms (22 and 24) and the spiral torsion spring system (70) is depicted in FIG. 9.

While FIGS. 7 and 8 illustrates a spiral torsion spring system 70, it would be understood that any other resilient component, including linear springs, or elastic threads or any other spring-based system could be used to implement similar functionality.

Figure 10:
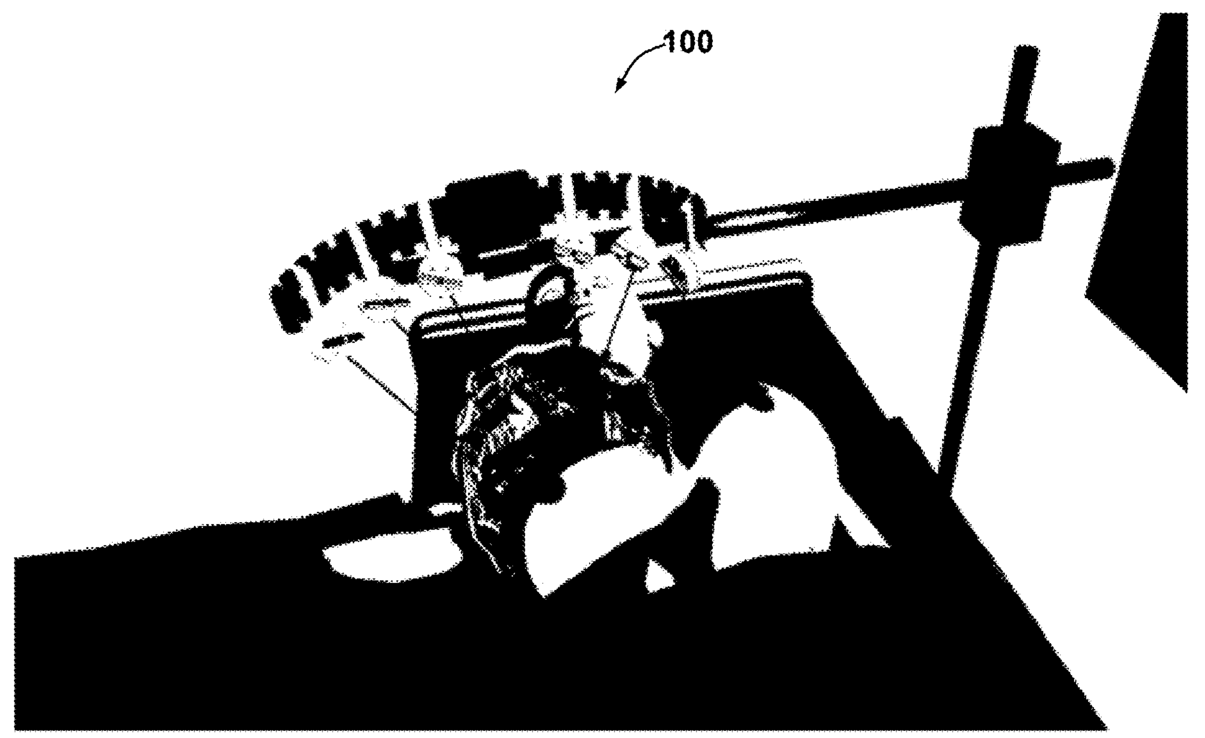
FIG. 10 illustrates use of the skin flap retraction device (100) of the present invention for skin flap retraction during surgery.

Working of the Invention: Referring to the FIG. 10, the skin flap retraction device (100) is illustrated to be mounted on the operating table from the assistant's end, using an elongated support arm which is preferably made of stainless steel, carbon fibre, titanium alloy, or the like.

A surgical incision is depicted over a patient's breast. An upper skin flap edge is illustrated as being retracted the spiral torsion spring system (70). Each of the elastic/rigid cable (82) is suspended from each of the plurality of notches or pitches (50) using a clip (72) of the spiral torsion spring system (70). Referring to FIG. 2, the skin flap retraction device (100) can be rotated about the base plate (36) and the surgery on a lower skin flap can be carried out with ease.

It would be understood that during the surgery, the skin flap retraction device (100) can provide continuous dynamic retraction for rising skin flaps during surgery. The skin flap retraction device (100) can be suspended from the assistant's end using a solid rod that can be attached to the operating table. The skin flap retraction device (100) enables the surgeon to perform the surgery irrespective of the size, shape, volume or laxity of an organ of interest in a safe manner without the necessity of the assistant surgeon. To achieve this, the malleable arms (22 and 24) can be bent in either an inward or an outward direction at any part of their length. This enables the surgeon to manipulate a size and an angle of the malleable arms (22 and 24) and thereby facilitating its use in almost all kinds of surgeries. The pre-curved detachable central solid block (20) provides the strength and stability to the skin flap retraction device (100). The skin flap retraction device (100) can be comfortably used in raising both the upper and lower skin flaps during mastectomy. To enable this, there is a peg and socket joint (62) provided at the base of a midpoint of the pre-curved detachable central solid block (20) which can be rotated about a shaft of the on the baseplate (36) which is also used to mount the skin flap retraction device (100) on the operating table. The skin flap retraction device (100) can provide dynamic and continuous traction by each of the elastic/rigid/cable (82) that are is passed from the spiral torsion spring system (70) attached to the plurality of notches or pitches (50) present on the upper and lower edges (52 and 54) of the malleable arms (22 and 24). The tension delivered to the skin flap can be dynamically changed by manipulating the torsion delivered by the spiral torsion spring system (70). The tension generated can be maintained as well as changed dynamically using the tension key (80) and the one or more unidirectional stoppers (83) that are provided in the spiral torsion spring system (70). As the rising of the skin flap progresses towards the skin flap retraction device (100), the spiral torsion spring system (70) recoils elastic/rigid cable (82) contracts and provides continuous traction in that direction. Thus, this obviates the need for a manual retraction by the assistant surgeon.

Based on the above, it will be understood that the skin flap retraction device (100) can be mounted on the assistant's end which is self-retaining and which doesn't require the assistant surgeons. The skin flap retraction device (100) has the malleable arms (22 and 24) that can be contoured to the size or shape of the organ of interest. The skin flap retraction device (100) can be rotated about the base plate (36) and can be used to operate on both the upper and the lower skin flaps. The skin flap retraction device (100) can be suspended directly above the operating field and so, vertical traction can be provided instead of horizontal traction. The skin flap retraction device (100) can provide uniform dynamic traction using each of the elastic/rigid cable (82) attached to the spiral torsion spring system (70) throughout the length of the skin flap that can help in rising flaps of adequate and uniform thickness.

Based on the above, it will be understood that the skin flap retraction device (100) of the present invention provides multiple advantages over prior art solutions, including: offering a self-retaining retraction system (which needs no assistant surgeon). enables uniform traction force that can be applied throughout the length of the skin flap at a given point of time; enables vertical traction can be applied by suspending the retractor directly above the surgical field; allowing the surgeon to operate freely from the other side (lower side when the upper flap is being raised) due to the arcuate shaped design; enabling suspension on the assistant surgeon's end; the malleable arm design with which the length can be modified based on the size and contour of the organ of interest; the dynamic spiral torsion system with which the length and tension delivered to the skin flap via the elastic/rigid cables can be dynamically manipulated.

While the exemplary embodiments of the present invention are described and illustrated herein, it will be appreciated that they are merely illustrative. It will be understood by those skilled in the art that various modifications in form and detail may be made therein without departing from or offending the spirit and scope of the invention as defined by the appended claims. Additionally, the invention illustratively disclose herein suitably may be practiced in the absence of any element which is not specifically disclosed herein—and in a particular embodiment that is specifically contemplated, the invention is intended to be practiced in the absence of any one or more element which are not specifically disclosed herein.

We claim:

1. A skin flap retraction device (100), comprising:

pre-curved detachable central solid block (20); and malleable arms (22 and 24) having a first malleable arm (22) and a second malleable arm (24), wherein an end (18) of the first malleable arm (22) is received in a first respective end (16) of the pre-curved detachable central solid block (20) and secured by a first coupling assembly (28) with a screw (32), and an end (26) of the second malleable arm (24) is received in a second respective end (14) of the pre-curved detachable central solid block (20) and secured by a second coupling assembly (30) with a screw (34), wherein each of the first and second malleable arms (22, 24) comprising:

a plurality of notches (50) disposed along an upper edge (52) and a lower edge (54) of the first and second malleable arms (22, 24); and a spiral torsion spring system (70) removably attachable to at least one notch of the plurality of notches (50), the spiral torsion spring system (70) comprising:

a torsion spring (76);

an elastic or rigid cable (82) attached to the torsion spring (76) at a first end of the elastic or rigid cable (82) and attached to a metallic hook (78) at a second end of the elastic or rigid cable (82) such that the elastic or rigid cable (82) is configured for engagement with subcuticular layer of skin;

a tension key (80) disposed on a flat surface (71) of the spiral torsion spring system (70) and configured to increase or decrease a tension in the torsion spring;

one or more unidirectional stoppers (83) disposed on the flat surface (71) and configured to maintain the tension by holding the tension key (80); and a split key (81) configured to be lifted and rotated to decrease the tension in the torsion spring (76).

2. The skin flap retraction device (100) as claimed in claim 1 wherein the malleable arms (22 and 24) is configured to be bent in any shape based on an organ shape or in a shape of an incision such that a retraction force is delivered to an area of interest from any desired angle or direction.

3. The skin flap retraction device (100) as claimed in claim 1 wherein the skin flap retraction device (100) is mounted on a base plate (36).

4. The skin flap retraction device (100) as claimed in claim 3 further comprises:

a rotatable shaft coupling system (38) having one or more rotational stoppers (35); and the base plate (36) configured to accommodate the rotatable shaft coupling system (38).

5. The skin flap retraction device (100) as claimed in claim 3 further comprising a body (56) and a socket (65) complementary to a peg (31) disposed on abase of the pre-curved detachable central solid block (20).

6. The skin flap retraction device (100) as claimed in claim 5 wherein the a position of the pre-curved detachable central solid block (20) with respect to the base plate (36) is held using the rotational stoppers (35) wherein the pre-curved detachable central solid block (20) is placed to face any direction by utilizing a peg and socket joint (62) disposed at a base of the pre-curved detachable central solid block (20).

* * * * *